US012102654B2

(12) United States Patent
Gai et al.

(10) Patent No.: US 12,102,654 B2
(45) Date of Patent: Oct. 1, 2024

(54) **PRODUCT DERIVED FROM *RHODOCOCCUS RUBER*, AND PHARMACEUTICAL USE THEREOF**

(71) Applicant: LIAONING GREATEST BIO-PHARMACEUTICAL CO. LTD., Benxi (CN)

(72) Inventors: Bo Gai, Benxi (CN); Chunyan Dou, Benxi (CN); Yi Zhang, Benxi (CN); Guoying Zhang, Benxi (CN)

(73) Assignee: Liaoning Greatest Bio-Pharmaceutical Co., Ltd., Benxi (CN)

( * ) Notice: Subject to any disclaimer, the term of this patent is extended or adjusted under 35 U.S.C. 154(b) by 426 days.

(21) Appl. No.: 17/421,717

(22) PCT Filed: Dec. 13, 2019

(86) PCT No.: PCT/CN2019/125180
§ 371 (c)(1),
(2) Date: Jul. 8, 2021

(87) PCT Pub. No.: WO2020/147472
PCT Pub. Date: Jul. 23, 2020

(65) Prior Publication Data
US 2022/0241348 A1    Aug. 4, 2022

(30) Foreign Application Priority Data

Jan. 15, 2019  (CN) .......................... 201910036001.4
Oct. 25, 2019  (CN) .......................... 201911022193.X (51) Int. Cl.
*A61K 35/74*    (2015.01)
*A61K 9/00*     (2006.01)
(Continued)

(52) U.S. Cl.
CPC ............ *A61K 35/74* (2013.01); *A61K 9/0014* (2013.01); *A61P 17/02* (2018.01); *A61P 31/20* (2018.01); *C12N 1/205* (2021.05); *C12R 2001/01* (2021.05)

(58) Field of Classification Search
CPC .......... A61K 35/74; A61P 17/02; C12N 1/205
See application file for complete search history.

(56) References Cited

FOREIGN PATENT DOCUMENTS

CA    2639129 A1 *  2/2009  ............. A61K 35/74
CN    1 879 661 A    12/2006
(Continued)

OTHER PUBLICATIONS

Wang, Yi, et al. "Nocardia rubra cell wall skeleton accelerates cutaneous wound healing by enhancing macrophage activation and angiogenesis." Journal of International Medical Research 46.6 (2018): 2398-2409. (Year: 2018).*
(Continued)

*Primary Examiner* — Louise W Humphrey
*Assistant Examiner* — Candice Lee Swift
(74) *Attorney, Agent, or Firm* — Rodney J. Fuller; BOOTH UDALL FULLER, PLC (57) ABSTRACT

Isolated *Rhodococcus ruber*, a product derived from the *Rhodococcus ruber* (in particular, a product derived from the *Rhodococcus ruber* cell wall), a method for preparing the product derived from the *Rhodococcus ruber*, and use of the product derived from the *Rhodococcus ruber* in prevention and/or treatment of lichen planus. The product derived from the *Rhodococcus ruber* effectively reduce the erosion area of lichen planus and relieve pain.

4 Claims, 2 Drawing Sheets

Specification includes a Sequence Listing.

Experimental group: Before treatment | After 2 weeks of treatment | After 4 weeks of treatment Control group: Before treatment | After 2 weeks of treatment | After 4 weeks of treatment (51) Int. Cl.
    A61P 17/02    (2006.01)
    A61P 31/20    (2006.01)
    C12N 1/20     (2006.01)
    C12R 1/01     (2006.01)

(56) References Cited

FOREIGN PATENT DOCUMENTS

| CN | 102895264 A    | 1/2013  |
| CN | 106591172 A    | 4/2017  |
| CN | 108815197 A    | 11/2018 |
| CN | 108938674 A *  | 12/2018 |
| CN | 109576180 A    | 4/2019  |
| EP | 1 547 607 A1   | 6/2005  |
| EP | 1 741 438 A1   | 1/2007  |

OTHER PUBLICATIONS

Mayo Clinic; https://www.mayoclinic.org/diseases-conditions/lichen-planus/symptoms-causes/syc-20351378; accessed Oct. 23, 2023 (Year: 2023).*

Medline Plus; https://medlineplus.gov/ency/article/003251.htm#:~:text=Lichenified%20means%20the%20skin%20has,used%20to%20treat%20lichenified%20skin.; accessed Oct. 23, 2023 (Year: 2023).*

Tokuzen, Reiko, et al. "Effect of Nocardia and Mycobacterium cell-wall skeletons on autochthonous tumor grafts." GANN Japanese Journal of Cancer Research 66.4 (1975): 433-435. (Year: 1978).*

Wang, Yi et al., "Nocardia rubra cell wall skeleton accelerates cutaneous wound healing by enhancing macrophage activation and angiogenesis", Journal of International Medical Research, 46(6):2398-2409 (2018).

Supplementary European Search Report for EP 19 91 0829 dated Nov. 25, 2022 (11 pages).

Garcia-Pola, Maria Jose et al., "Treatment of oral lichen planus. Systematic review and therapeutic guide", Med Clin (Barc), 149(8):351-362 (Oct. 23, 2017).

Lodi, Giovanni et al., "Current controversies in oral lichen planus: Report of an international consensus meeting. Part 2. Clinical management and malignant transformation", Oral Surg Oral Med Oral Pathol Oral Radiol Endod, 100:164-178 (Aug. 2005).

Oray, Merih et al., "Long-term side effects of glucocorticoids", Expert Opin Drug Saf., 15(4):457-465 (2016) English abstract only.

Gein, Sergey et al., "In vitro cytokine stimulation assay for glycolipid biosurfactant from Rhodococcus ruber: Role of monocyte adhesion", Cytotechnology, 63:559-566 (2011).

You, Xiaona et al., "Study on the identification of the production strain about N-CWS, Chinese Journal of Bioprocess Engineering", 11(4):55-58 (Jul. 2013) English abstract only.

Li, Jie-ting et al., "Development of study on treatment for oral lichen planus", Chinese Journal of Practical Stomatology, 3(3):179-182 (Mar. 31, 2010).

Usatine, Richard P., Md, et al., "Diagnosis and Treatment of Lichen Planus", American Family Physician, 84(1):53-60 (Jul. 1, 2011).

* cited by examiner

PRODUCT DERIVED FROM *RHODOCOCCUS RUBER*, AND PHARMACEUTICAL USE THEREOF

CROSS REFERENCE TO RELATED APPLICATIONS

This application is the U.S. National Stage of International Application No. PCT/CN2019/125180, filed on Dec. 13, 2019, which claims the priority of Chinese patent application "*Rhodococcus ruber* cell wall skeleton and use thereof" filed on Jan. 15, 2019 (application No. 201910036001.4) and the priority of Chinese patent application "An isolated *Rhodococcus ruber*" filed on Oct. 25, 2019 (application No. 201911022193.X), their entire contents of which are incorporated herein by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 2,226 byte ASCII (text) file named "Sequencelisting_719098CPUS" created on Dec. 13, 2019.

BIOLOGICAL DEPOSIT OF *RHODOCOCCUS RUBER* ACCESSION NO. 17431

A Biological Deposit of *Rhodococcus Ruber* Accession No. 17431 was made at the China General Microbiological Culture Collection Center (CGMCC) (Yard No. 1 (3) West Beichen Road, Chaoyang District, Beijing, Institute of Microbiology, Chinese Academy of Sciences; postal code: 100101), on Mar. 22, 2019, under the provisions of the Budapest Treaty, and assigned by the International Depositary Authority the Accession No. 17431. Upon issuance of a patent, all restrictions upon the Deposit will be irrevocably removed, and the Deposit is intended to meet the requirements of 37 CFR §§ 1.801-1.809. The Deposit will be maintained in the depository for a period of 30 years, or 5 years after the last request, or for the effective, enforceable life of the patent, whichever is longer, and will be replaced, if necessary, during that period; and the requirements of 37 CFR §§ 1.801-1.809 are met.

FIELD OF THE INVENTION

The present disclosure relates to the fields of medicine, microbiology and biopharmacy. Specifically, it relates to *Rhodococcus ruber* and cell wall components, formulations, pharmaceutical compositions, preparation methods thereof, and components from *Rhodococcus ruber* cell wall for using in treatment.

BACKGROUND OF THE INVENTION

*Rhodococcus ruber* is a gram-positive bacterium. Generally speaking, its colony is orange-yellow or orange-red in color, and round in shape; the size of the colony is about 1 mm to 2 mm; the cell morphology is spherical or short rod-shaped; it can form primary branched mycelium; and it has no flagella. *Rhodococcus ruber* is aerobic and chemically heterotrophic.

At present, researchers have performed whole gene sequencing for *Rhodococcus ruber*. For example, Fan Xin et al. sequenced the whole genome of *Rhodococcus ruber* SD3 strain and performed bioinformatic analysis. The whole genome length of the SD3 strain is about 5.37 Mb, the GC content is about 70.63%, and the GenBank accession number is CP029146 (Fan Xin, Whole-genome sequencing and expression analysis of heat shocking protein DnaK from *Rhodococcus ruber* SD3, Genomics and Applied Biology, January 2019).

The genus *Rhodococcus* can adapt to a variety of living environments due to its strong tolerance to organic substances and its wide degradation spectrum. Therefore, *Rhodococcus* is widely used in the fields of pollution remediation, organic compound degradation, sewage treatment, etc. At present, the main application field of *Rhodococcus ruber* lies in environmental management, see CN108862590A, CN107151635A, CN102250796A, CN1519312A, CN103627653A, CN101033454A, CN108130288A, CN104830738A, CN101619299A, CN103509833A, CN106434466A, CN101580808A, CN102604875A, CN103160491A, CN106591168A, CN106591172A and CN105820982A.

CN109576180A discloses a bacterium RDC-01 screened from the red soil in the suburbs near Panyu District, Guangzhou. After 16S rRNA gene sequence analysis and cultivation characteristics identification, the strain was identified as *Rhodococcus* Tuber. After inactivation, the bacterium was added to an inactivated vaccine for animals as an immune adjuvant, and it was found to be able to promote the production of antibodies in animals.

However, the application of *Rhodococcus ruber* in the field of medicine in human has not yet been reported.

Oral lichen planus (OLP) is a chronic inflammatory disease of the skin and mucosa mediated by cellular immunity (Oral and Mucosal Diseases, Peking University Medical Press, 2014). It is quite common clinically, with a prevalence of 0.1% to 4%. Long-term erosion of oral lichen planus has a potential risk of malignant transformation (Lodi G et al., Current controversies in oral lichen planus: Report of an international consensus meeting, part 2; clinical management and malignant transformation. Oral Surgery Oral Medicine Oral Pathology Oral Radiology and Endodontics, 2005, 100(2):164-78). In 2005, OLP was classified by WHO as oral potentially malignant disorders (OPMD). The latest study in 2019 showed that the malignant transformation rate of OLP was 0.8% to 1.5%.

The diagnosis of lichen planus can refer to the "Guidelines for the diagnosis and treatment of oral lichen planus" issued by the Oral Mucosal Disease Professional Committee of the Chinese Stomatological Association and the Professional Committee of Integrated Chinese and Western Medicine of the Chinese Stomatological Association, or refer to the WHO 2003 diagnostic criteria for oral lichen planus. According to "Oral and Mucosal Diseases", OLP can be divided into reticular, annular, linear, papular, erosive, plaque-like, bullous and atrophic type.

The cause of OLP is yet unknown and the course of the disease is prolonged and relapsed. There is no radical therapy yet, and most treatments focus on symptomatic and immunomodulatory treatments. Clinically, topical use of glucocorticoids is the first-line therapy (García-Pola M J et al., Treatment of oral lichen planus. Systematic review and therapeutic guide. Medicina Clínica, 2017, 149(8):351-362), and short-term systemic administration of glucocorticoids or immunosuppressive agents can be applied to severe patients. However, topical and long-term administration of glucocorticoids has relatively great side effects, such as causing a series of complications including mucosal atrophy, aggravating infections, etc., systemic adverse reactions such as electrolyte imbalance, delayed wound healing, and growth inhibition of children, etc. Therefore, such agents should not be for long-term clinical administration (Oray M et al., Long-term side effects of glucocorticoids. Expert Opinion on Drug Safety, 2016, 15(4):457-65).

Therefore, development of a safe and effective medicament without obvious side effects is an urgent clinical problem to be solved.

SUMMARY OF THE INVENTION

According to some embodiments of the present disclosure, in one aspect, an isolated *Rhodococcus ruber* is provided.

According to some particular embodiments of the present disclosure, a *Rhodococcus ruber* is provided, which was deposited at China General Microbiological Culture Collection Center (CGMCC) on Mar. 22, 2019 (Yard No. 1(3) West Beichen Road, Chaoyang District, Beijing, Institute of Microbiology, Chinese Academy of Sciences; postal code: 100101), under deposit number CGMCC No. 17431. The deposit meets the requirements of the Budapest Treaty on the International Recognition of the Deposit of Microorganisms for the Purposes of Patent Procedure.

According to some embodiments of the present disclosure, *Rhodococcus ruber* and derivative products thereof are provided. The derivative products are derived from *Rhodococcus ruber* and comprise the components of *Rhodococcus ruber* (such as proteins, nucleic acids, lipids, cell walls and components thereof, carbohydrates or metabolites).

In particular embodiments, an isolated *Rhodococcus ruber* cell wall is provided.

In particular embodiments, an isolated *Rhodococcus ruber* cell wall is provided, and the *Rhodococcus ruber* is the strain under the deposit number of CGMCC No. 17431.

In particular embodiments, an isolated *Rhodococcus ruber* cell wall skeleton is provided.

In particular embodiments, an isolated *Rhodococcus ruber* cell wall skeleton is provided, and the *Rhodococcus ruber* is the strain under the deposit number of CGMCC No. 17431.

According to some embodiments of the present disclosure, a pharmaceutical composition is provided, which comprises *Rhodococcus ruber* cell wall or *Rhodococcus ruber* cell wall skeleton according to the present disclosure.

According to some embodiments of the present disclosure, a product derived from *Rhodococcus ruber* is provided, which comprises a product obtained by disruption of *Rhodococcus* Tuber.

According to some other embodiments of the present disclosure, a product derived from *Rhodococcus ruber* is provided, which comprises a product obtained by disruption and purification (removing lipids, nucleic acids and proteins) of *Rhodococcus ruber*.

According to some other embodiments of the present disclosure, a product derived from *Rhodococcus ruber* is provided, which comprises *Rhodococcus ruber* cell wall.

According to some other embodiments of the present disclosure, a product derived from *Rhodococcus ruber* is provided, which comprises *Rhodococcus ruber* cell wall skeleton.

According to some embodiments of the present disclosure, a pharmaceutical composition or a medical device is provided, which comprises a product obtained by disruption of *Rhodococcus ruber*.

According to some other embodiments of the present disclosure, a pharmaceutical composition or a medical device is provided, which comprises a product obtained by disruption and purification (removing lipids, and/or nucleic acids, and/or proteins) of *Rhodococcus* Tuber.

According to some other embodiments of the present disclosure, a pharmaceutical composition or a medical device is provided, which comprises *Rhodococcus ruber* cell wall.

According to some other embodiments of the present disclosure, a pharmaceutical composition or a medical device is provided, which comprises *Rhodococcus ruber* cell wall skeleton.

According to some other embodiments of the present disclosure, a pharmaceutical composition or a medical device is provided, which comprises the product derived from *Rhodococcus ruber* as described above.

In particular embodiments, the pharmaceutical composition further comprises a pharmaceutically acceptable excipient.

In some embodiments of the pharmaceutical composition, the product derived from *Rhodococcus ruber* is 1 part by weight, and the pharmaceutically acceptable excipient is 200 to 300 parts by weight (for example, 200, 210, 220, 230, 240, 250, 260, 270, 280, 290, 300 and any value within the range between any two numbers above).

In some other embodiments of the pharmaceutical composition, the *Rhodococcus ruber* cell wall is 1 part by weight, and the pharmaceutically acceptable excipient is 200 to 300 parts by weight (for example, 200, 210, 220, 230, 240, 250, 260, 270, 280, 290, 300 and any value within the range between any two numbers above).

In still other embodiments of the pharmaceutical composition, the *Rhodococcus ruber* cell wall skeleton is 1 part by weight, and the pharmaceutically acceptable excipient is 200 to 300 parts by weight (for example, 200, 210, 220, 230, 240, 250, 260, 270, 280, 290, 300 and any value within the range between any two numbers above).

In some embodiments, the pharmaceutical composition can be prepared as a liquid (liquid formulation).

In some other embodiments, the pharmaceutical composition can be prepared as a solid (dry powder formulation or lyophilized powder formulation).

The skilled person understands that, for the pharmaceutical composition of the present disclosure, the liquid formulation and the dry powder formulation (or lyophilized powder formulation) can be converted into each other, and the difference lies only in the water content. A dry powder formulation (or lyophilized powder formulation) is obtained by removing most or all of the water from the liquid formulation. A liquid formulation is obtained by dissolving (or reconstituting) the dry powder formulation (or lyophilized powder formulation).

In some embodiments, the medicament or the pharmaceutical composition is prepared into a dosage form selected from the group consisting of ointment, cream, gel, lotion, tincture, liniment, oil, paste, aerosol, buccal tablet, patch, lyophilized powder and suspension.

In some embodiments, the dosage form is a buccal tablet. For example, it can be prepared by pressing the lyophilized powder.

In some embodiments, the pharmaceutically acceptable excipient relates to, but is not limited to: filler, stabilizer, flavoring agent, disintegrant, binder and lubricant.

According to some embodiments of the present disclosure, a method for the preparation of products derived from

*Rhodococcus ruber* is provided, which comprises or consists of the following steps:
1) providing *Rhodococcus ruber*;
2) optionally, culturing the *Rhodococcus ruber*;
3) optionally, collecting the cultured *Rhodococcus ruber*;
4) disrupting the cultured *Rhodococcus ruber* to obtain a disrupted product;
5.1) optionally, removing lipids from the disrupted product;
5.2) optionally, removing nucleic acids from the disrupted product;
5.3) optionally, removing proteins from the disrupted product;
5.4) obtaining a purified product;
6) optionally, removing the water from the purified product, preferably removing the water from the purified product by lyophilization;
7) optionally, performing aliquoting;
8) harvesting the product derived from *Rhodococcus ruber*;
wherein, steps 5.1), 5.2) and 5.3) are interchangeable in order or performed in parallel; step 6) and step 7) are interchangeable in order or performed in parallel.

Optionally, step 5) can further comprising a step of removing the cell membranes (for example, using a non-ionic surfactant).

Culture of *Rhodococcus ruber* is not limited to particular culture medium and culture parameters, and the skilled person can use well-known and appropriate methods for cultivation, and can use petri dishes, culture flasks and fermenters according to the preparation scale.

For the disruption of *Rhodococcus ruber*, the purpose is to remove the substances in the cells, so ultrasonication, lysozyme and other technologies can be used. The skilled person understands that any known or future method suitable for disrupting gram-positive bacteria is suitable for the technical solution of the present disclosure.

The skilled person has the ability to adjust the particular parameters and equipment for culture, disruption, separation, collection, removal of impurity, and aliquoting according to the subsequent application (such as oral administration, injection, topical application, etc.) of the active ingredients (cell walls and components thereof), so as to avoid introducing factors that affect subsequent applications in the preparation steps.

In some embodiments, an organic solvent is used to remove lipids from the disrupted product. In some embodiments, a nuclease is used to remove DNA and RNA from the disrupted product. In some embodiments, a hydrolase is used to degrade proteins in the disrupted product. In some embodiments, a surfactant is used to remove cell membranes from the disrupted product.

In some embodiments, the average particle size of disruption is 10 nm to 1000 nm; 10, 20, 30, 40, 50, 60, 70, 80, 90, 100, 110, 120, 130, 140, 150, 160, 170, 180, 190 nm 10 nm, and the range between any two of the above values can be mentioned. There are many methods for measuring particle size (Hu Songqing et al., Modern technology of particle size measurement, Modern Chemical Industry, 2002, 22:1).

In some particular embodiments, the average particle size of disruption is 10 nm to 800 nm.

In some other particular embodiments, the average particle size of disruption is 10 nm to 500 nm.

In some other particular embodiments, the aliquoting refers to aliquoting into containers. The container is selected from the group consisting of vial, tube, package, bag, plate, ampoule, injection device, aluminum film packaging, dressing and capsule.

For example, in particular embodiments, the aliquoting refers to aliquoting into vials/ampoules. Solvent is added to the vials/ampules just before use.

According to some embodiments of the present disclosure, a product derived from *Rhodococcus ruber* is provided, which is obtained by the preparation method of the present disclosure.

According to some embodiments of the present disclosure, a pharmaceutical composition or a medical device is provided, which comprises a product derived from *Rhodococcus ruber* obtained by the preparation method of the present disclosure.

According to some embodiments of the present disclosure, an isolated *Rhodococcus ruber* cell wall is provided, which is useful for the prevention and/or treatment of lichen planus.

According to some embodiments of the present disclosure, a product derived from *Rhodococcus ruber* is provided, which is useful for the prevention and/or treatment of lichen planus.

According to some embodiments of the present disclosure, a pharmaceutical composition or a medical device is provided, which is useful for the prevention and/or treatment of lichen planus.

According to some embodiments of the present disclosure, the use of the *Rhodococcus ruber* cell wall according to the present disclosure in the prevention and/or treatment of lichen planus is provided; the use of the *Rhodococcus ruber* cell wall according to the present disclosure in the preparation of a medicament/medical device for the prevention and/or treatment of lichen planus is also provided.

According to some embodiments of the present disclosure, use of the product derived from *Rhodococcus ruber* according to the present disclosure in the prevention and/or treatment of lichen planus is provided; use of the product derived from *Rhodococcus ruber* according to the present disclosure in the preparation of a medicament/medical device for the prevention and/or treatment of lichen planus is also provided.

According to some embodiments of the present disclosure, use of the pharmaceutical composition according to the present disclosure in the prevention and/or treatment of lichen planus is also provided; use of the pharmaceutical composition according to the present disclosure in the preparation of a medicament/medical device for the prevention and/or treatment of lichen planus is also provided.

According to some embodiments of the present disclosure, use of any one selected from the following in the preparation of a medicament (or medical device) is provided: *Rhodococcus ruber* according to the present disclosure, the isolated *Rhodococcus ruber* cell wall according to the present disclosure, the product derived from *Rhodococcus ruber* according to the present disclosure and the pharmaceutical composition according to the present disclosure.

In some particular embodiments, the medicament is used for the prevention and/or treatment of lichen planus.

In some particular embodiments, the medical device (such as dressing, patch, bandage, film, etc.) is used for the prevention and/or treatment of lichen planus.

According to some embodiments of the present disclosure, a method for the prevention and/or treatment of lichen planus is also provided, comprising exposing a subject to a therapeutically effective amount (or a prophylactically effective amount) of any one selected from of the following:

the *Rhodococcus ruber* according to the present disclosure, the isolated *Rhodococcus ruber* cell wall according to the present disclosure, the product derived from *Rhodococcus ruber* according to the present disclosure, the pharmaceutical composition according to the present disclosure, the medical device according to the present disclosure.

In some particular embodiments, the average period of exposure lasts for 2 days to 2 months. Specifically, for example, 2, 4, 6, 8, 10, 15, 20, 25, 30, 35, 40, 45, 50, 55 and 60 days; for another example, 1, 2, 3, 4 and 5 weeks can be mentioned. In particular embodiments, the active ingredient is administrated to the subjects for 4 weeks.

In some embodiments, the administration is performed at a frequency selected from the group consisting of: administrating for 1 to 3 times per day, 1 to 6 times in two days, 1 to 9 times in three days, 1 to 14 times per week, 1 to 60 times per month. In some embodiments, the active ingredient is administrated for twice a day, once a day, or once every two days.

The amount of each administration refers to a different dosage depending on the particular conditions of the subject, usually 1 μg to 1000 μg/unit dose/each administration; specifically, such as 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200 μg/unit dose/each administration, and the range between any two of the above values.

In some particular embodiments, the exposure is achieved by the following ways, such as but not limited to: oral, intravenous, intramuscular, percutaneous, transdermal, intraperitoneal, puncture, nasal spray, eye drops or suppository.

In some particular embodiments, the subject is an animal other than human, such as farm animals, pets, working animals, ornamental animals and production animals.

In particular embodiments, the subject is a human.

In some particular embodiments, the subject is suspected of having, confirmed to have, has suffered from, or is susceptible to the target disease or symptoms thereof.

In the context of the present application, the only therapeutic (or prophylactical) active ingredient in the medicament or the pharmaceutical composition is a product derived from *Rhodococcus ruber*, notably comprising components of *Rhodococcus ruber* (such as proteins, nucleic acids, lipids, cell walls and components thereof, carbohydrates or metabolites); in particular, products comprising *Rhodococcus ruber* cell wall (more preferably *Rhodococcus ruber* cell wall skeleton or components thereof).

DETAILED DESCRIPTION OF EMBODIMENTS OF THE INVENTION

"Isolation" refers to the separation of the *Rhodococcus ruber* of the present disclosure from its original growth environment.

The skilled person knows that the cell wall structures of gram-positive bacteria and gram-negative bacteria are different. Specifically, the cell wall of gram-positive bacteria is thicker (usually 20 nm to 80 nm), comprising about 90% peptidoglycan and about 10% teichoic acid (a polymer formed by alcohol and phosphoric acid molecules, usually existing in the form of sugar ester or amino acid ester). The peptidoglycan layer is dense, even as many as 20 layers. However, the cell wall of gram-negative bacteria is much thinner than that of gram-positive bacteria, and the structure is more complex, divided into outer membrane and peptidoglycan layer (usually 2 nm to 3 nm).

The peptidoglycan layer is a unique component of the bacterial cell wall and is a derivative of heteropolysaccharide. Each peptidoglycan monomer comprises 3 parts: the sugar unit (for example, at least two sugar molecules are connected by glycosidic bonds to form the framework of peptidoglycan), the peptide tail (a short peptide chain formed by linking several amino acids, which is connected to a N-acetylmuramic acid molecule), and the peptide bridge (crosslinking adjacent "peptide tails" to form a high-strength network structure). Different bacteria have different peptide bridges, peptide tails and cross-linking manners.

Isolated *Rhodococcus ruber* Cell Wall Skeleton

In the present disclosure, "isolated *Rhodococcus ruber* cell wall" can be interpreted as either a complete cell wall or an incomplete cell wall (for example, disrupted or partially degraded). Under the teaching of the present disclosure, the skilled person will understand that the components exhibiting the desired activity are derived from *Rhodococcus ruber* cell wall (for example, the cell wall itself or components thereof). Therefore, various forms are allowed to be used in clinical applications, including complete cell walls, disrupted cell walls, incomplete degradation products of cell walls, cell wall components, cell wall extracts, etc., which are all included in the scope of the present disclosure.

Cell Wall Skeleton

A component that constitute the main structure of the cell wall; however, it cannot be interpreted as merely representing the cross-linked network-like entity in the cell wall, and the skilled person understands that other cell wall components adsorbed on, bound to and carried by the cross-linked network-like entity are not excluded.

*Rhodococcus ruber*

The *Rhodococcus ruber* used in the embodiments of the present disclosure refers to the *Rhodococcus ruber* species of the *Rhodococcus* genus, and is not limited to a particular cell strain.

Non-limiting examples include the TOY7 strain (Agricultural Environment Microbiological Culture Collection, Nanjing Agricultural University), CGMCC No. 4795, DSM43338, CCTCC No. 2012035, CGMCC No. 16640 and CGMCC No. 17431.

Identification of *Rhodococcus ruber*

According to known or future microbial identification techniques, the skilled person can perform taxonomic identification on a strain of bacteria. For example, the available identification techniques include morphology, physiological and biochemical characteristics, 16S rRNA, and the like. The skilled person understands that with the development of science and technology, identification techniques involve different methods. In the earlier period, morphological and biochemical identification methods were mainly used, but the reliability of these methods is not high. After the advent of sequencing technology, the skilled person can identify bacteria strains in a more reliable way. For example, when the DNA sequences of 16S rRNA are identified as having more than 97% (inclusive) of identity, two bacteria would be deemed as belonging to the same species (Hua Gougen et al., The taxonomy and application of *Rhodococcus*, Microbiology China, 2003: 30 (4)). In terms of *Rhodococcus ruber*, the known strains deposited in international (or national) collection authorities of strains are used as model strains, and the strains to be identified are compared with the model strains.

Dosage Form

The medicament or pharmaceutical composition or active ingredient or product of the present disclosure can be formulated into, but not limited to, the following forms: ointment, cream, plaster, gel, lotion, tincture, liniment, oil, paste, lyophilized powder, aerosol, suppository, patch, suspension, oral solution, buccal tablet and skin care product (cleanser, toning lotion, serum, lotion, cream and mask).

Excipient

An excipient suitable for the present disclosure is for example but not limited to: dextran, lactose, microcrystalline cellulose, trehalose, glycine, xylitol, sodium carboxymethyl cellulose, erythritol, gelatin, magnesium stearate, propellant, humectant, solvent, solubilizer, emulsifier, antioxidant, pH regulator and preservative. Specifically, non-limiting examples also include: albolene, carbomer, hydroxypropyl methylcellulose, methyl cellulose, sodium hydroxymethyl cellulose, chitosan, sucralfate chitosan, polyvinylpyrrolidone, polyvinyl alcohol, sodium hyaluronate, dimethyl ether, tetrafluoroethane, hydrofluoroalkane, glycerin, propylene glycol, deionized water, water for injection, distilled water, ethanol, hexadecanol, octadecanol, p-aminobenzoic acid, acetamide, isopropanol, Tween, polyoxyethyl hydrogenated castor oil, stearic acid, glyceryl monostearate, triglycerol monostearate, sucrose fatty acid ester, sucrose ester, sucrose acetate isobutyrate, sorbitan tristearate, isopropyl myristate, cholesterol, squalene, squalane, n-butanol, ethylene glycol, ethanol, propylene glycol, polyglycerol ester, sulfite, cysteine, di-tert-butyl hydroxytoluene, potassium sorbate, phosphate buffer solution, triethanolamine, sodium hydroxide, ethylenediamine, laurylamine, sodium bicarbonate, hydrochloric acid, nipagins, thimerosal, chlorocresol, trichlorobutanol, benzoic acid and sodium salt thereof.

Formulation Unit

The medicament or pharmaceutical composition or active ingredient or product of the present disclosure can be prepared in the form of a formulation unit.

In some embodiments, the unit dose of the medicament (or formulation, or therapeutic agent, or medical device) comprises:

0.001 mg to 500 mg of the *Rhodococcus ruber* product; or 0.001 mg to 500 mg of the *Rhodococcus ruber* cell wall; or 0.001 mg to 500 mg of the *Rhodococcus ruber* cell wall skeleton.

Particular examples of the unit dose are 0.001, 0.005, 0.01, 0.05, 0.1, 0.2, 0.3, 0.4, 0.5, 0.6, 0.7, 0.8, 0.9, 1, 2, 5, 10, 15, 20, 25, 30, 40, 50, 60, 70, 80, 90, 100, 150, 200, 250, 300, 350, 400, 450, 500 mg±10%, and the ranges between any two of the above values.

"Administrating", "administrated", "providing . . . to" and "treating", when applied to animals, humans, cells, tissues, organs or biological samples, refer to the contact of the medicament or medical device with the animals, humans, cells, tissues, organs or biological samples.

"Treatment" means administrating an internal or external medicament (therapeutic agent, active ingredient or composition) (such as the *Rhodococcus ruber* cell wall or pharmaceutical composition thereof according to the present disclosure) or a medical device to a subject, in order to alleviate (relieve, delay, improve, cure) one or more disease symptoms to a clinically measurable degree in the subject to be treated (or population thereof), wherein the subject has, is suspected of having, or is susceptible to one or more diseases or symptoms thereof.

The amount of the medicament (therapeutic agent, active ingredient or composition) that can effectively alleviate any disease symptoms is called the therapeutically effective amount. It can vary depending on a variety of factors, such as the disease state, age and body weight of the subject. It should be understood that the medicament (therapeutic agent, active ingredient or composition) may be ineffective in alleviating the target disease or symptoms thereof of a single subject, but is statistically effective for the target disease or symptoms thereof according to any statistical test method known in the art (such as Student's t test, chi-square test and U test according to Mann and Whitney).

The term "optionally" means, the event that follows this term can happen, but not necessarily happen; it depends on the situation. For example, "optionally, performing aliquoting" means that the product is allowed to be aliquoted, but it is not necessarily to be aliquoted; whether the product is aliquoted or not does not affect the realization of the technical effects.

"A/an", "one", "single" and "the", if not explicitly stated, also involve the plural forms.

The present disclosure is further described below with reference to the examples, preparation examples and test examples. However, these examples, preparation examples and test examples do not limit the scope of the present disclosure. When the particular conditions are not specified, operation should be performed in accordance with the normal conditions and the conditions recommended by the raw material supplier. The reagents without giving particular sources are conventional reagents purchased on the market.

The skilled person especially understands that although a specific cell line is used in the following particular examples, the realization of the technical effects does not depend on the specific cell line; any species belonging to the *Rhodococcus* genus, *Rhodococcus ruber* species is applicable.

EXAMPLES

Example 1. Deposition of the Strain

The original place for the isolation of the strain cannot be verified. The inventors deposited the laboratory-preserved seed strain at China General Microbiological Culture Collection Center (CGMCC, Yard No. 1(3) West Beichen Road, Chaoyang District, Beijing) on Mar. 22, 2019, under deposit number CGMCC No. 17431. Test showed that the deposited strain was viable.

Example 2. Identification of the Strain

1. Visual Observation of the Morphological Characteristics of the Colony

Figure 1:
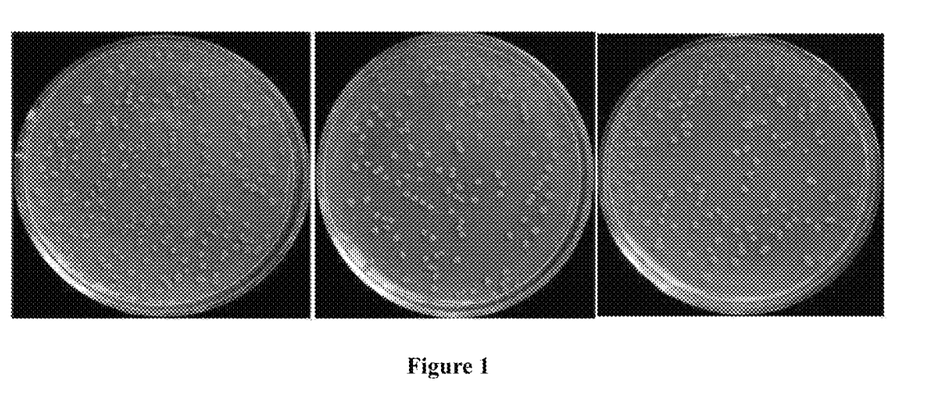
FIG. 1: The colony morphology of *Rhodococcus ruber*.

The strain was cultured on a glycerol agar medium at 30° C. to 37° C. (specifically 32° C. to 35° C.) for 12 to 72 (specifically 36 to 60, such as 40 to 50) hours, and the following was observed (FIG. 1):

the colonies plumped up;

were orange-red in color (slightly different depending on influences of light, the color of the culture medium, etc.);

the surface was dry and wrinkled, slightly shiny (slightly different depending on differences in culture conditions);

were fragile to touch;

the colony size was about 1 mm to 2 mm (slightly different depending on differences in culture conditions).

2. Microscope Observation

The hyphae grew in a branching structure with septate, and formed mycelium (slightly different depending on differences in culture conditions);

Division of the hyphae formed regular short and thick cells (slightly different depending on differences in culture conditions);

After culturing for 4 to 5 days, the hyphae became short rod-shaped or spherical (slightly different depending on differences in culture conditions).

3. Staining Property

The strain was gram stain positive.

4. Biochemical Reactions

The strain was cultured on a glycerol agar slant medium at 30° C. to 37° C. (specifically 32° C. to 35° C.) for 12 to 72 (specifically 36 to 60, such as 40 to 50) hours. Then, the following tests were performed on the culture.

4.1 Acid Production from Carbohydrates:

Positive: glycerin, mannitol, sorbitol, D-arabitol, D-fructose and D-glucose;

Negative: inositol, inulin, lactose, sucrose, starch, maltose, glycogen, xylitol, gluconate, trehalose, erythritol, melezitose, melibiose, raffinose, cellobiose, amygdalin, gentiobiose, adonol, arbutin, D-arabinose, L-arabinose, α-methyl-D-glucoside, α-methyl-D-mannoside, D-ribose, D-xylose, L-xylose, N-acetyl-glucosamine, D-turbiose, D-lyxose, β-methyl-D-xyloside, D-galactose, D-tagatose, D-fucose, L-fucose, D-mannose, L-sorbose, L-arabinitol, L-rhamnose and 2-keto-gluconate.

4.2 Enzyme Activity Determination (API ZYM):

Positive: alkaline phosphatase, lipid esterase (C8), lipase (C14), leucine araminase, valine araminase, cystine araminase, trypsin, chymotrypsin, acid phosphatase, naphthol-AS-B1-phosphohydrolase and α-glucosidase;

Negative: N-acetyl-glucosaminidase, esterase (C4), β-galactosidase, β-uronidase, β-glucosidase, α-galactosidase, α-mannosidase and β-fucosidase.

4.3 Nitrate Reduction Reaction: Positive, Catalase: Positive, Tyrosinase: Positive, Amylase: Negative, Oxidase: Negative, Gelatin Liquefaction: Negative.

4.4 Sole Carbon Source:

Biolog Gen II Positive for: glucuronamide, β-hydroxy-DL butyric acid, growth experiment: D-fructose-6-phosphate, α-D-glucose, D-fructose, D-mannitol, D-arabitol, D-sorbitol, quinic acid, γ-aminobutyric acid, citric acid, L-malic acid, bromosuccinic acid, Tween 40, propionic acid and acetic acid;

Biolog Gen III Sensitive to: dimethylamine tetracycline, sodium tetradecyl chemical sensitivity sulfate, rifamycin SV, pH 5.0, 8% sodium chloride, lincomycin, experiment fusidic acid, D-serine, vancomycin, tetrazolium violet and tetrazolium blue;

Tolerate to: sodium bromate, 1% sodium lactate, pH 6.0, 1%-4% sodium chloride, nalidixic acid, lithium chloride, potassium tellurite, aztreonam and sodium butyrate.

4.5. 16S rRNA Identification

Figure 2:
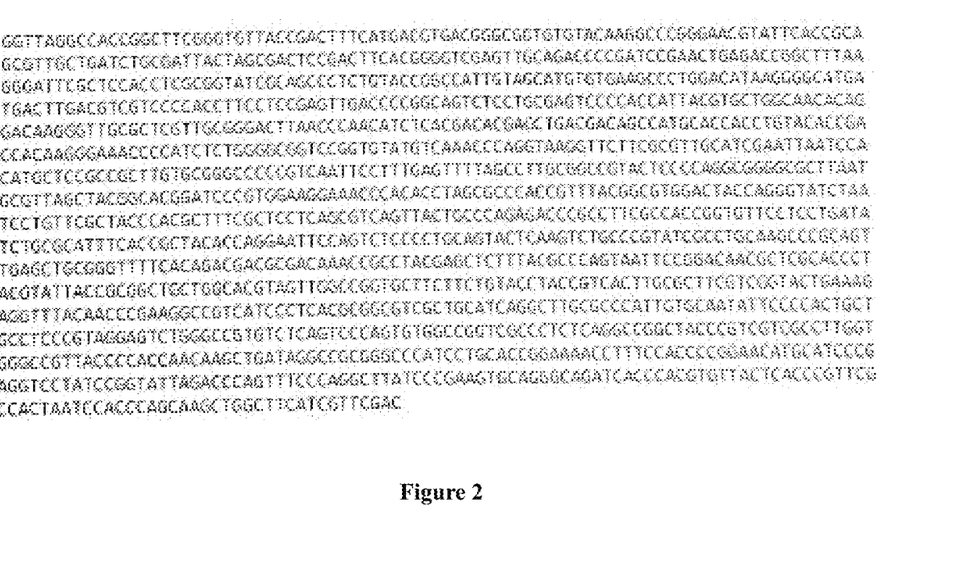
FIG. 2: The identification results of 16S rRNA.
Figure 3:
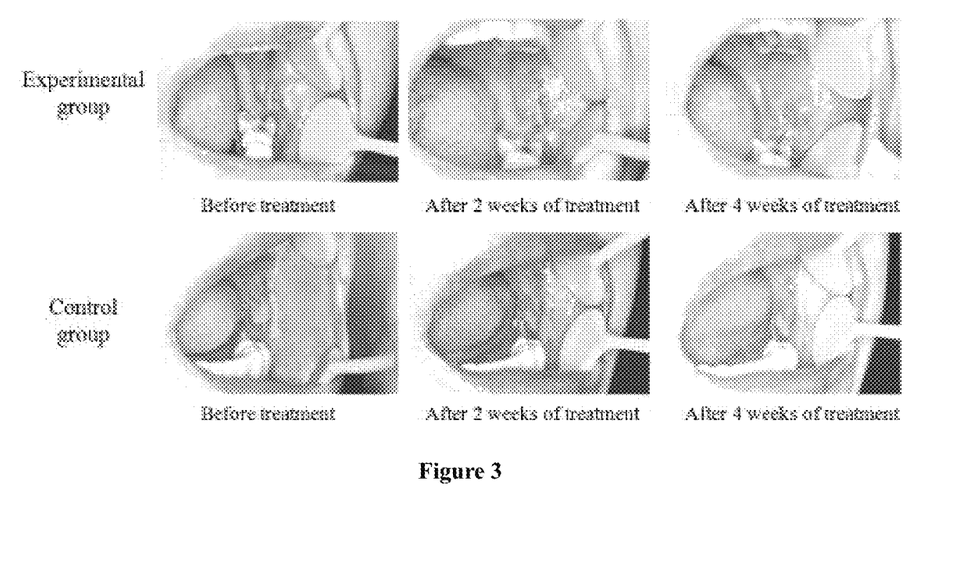
FIG. 3: The therapeutic effect of lichen planus.

The 15 strains isolated from the working seed tube and the 10 different strains isolated from the original seed tube were subjected to genome extraction, 16S rRNA amplification and sequencing. The 16S rRNA gene identity of the 25 strains in total was 100%. This means that the 25 strains are of the same species (FIG. 2).

Further, the neighbor-joining strain phylogenetic tree constructed based on the Kimura2-parameter algorithm showed that the strain was classified as *Rhodococcus* Tuber.

PREPARATION EXAMPLES

Preparation Example 1. Culture Methods

1. *Rhodococcus ruber* can be cultured by conventional microbial production methods.

2. The culture method can be solid culture or liquid culture.

3. There are no special requirements on the nutrient sources in the culture medium. The culture medium can contain carbon sources, nitrogen sources and other nutrient sources that are commonly used for microbial culture.

The carbon source can be any carbon source that can be consumed by *Rhodococcus ruber*, for example, fructose, glucose, and the like.

The nitrogen source can be broth, peptone, ammonium salt, nitrate and other organic or inorganic nitrogen-containing compounds.

For other nutrient sources, some inorganic salts can be added appropriately, for example, NaCl and phosphates.

4. There are no strict limitations on the culture conditions (temperature, time, etc.). The skilled person can choose the conditions that maximize the yield based on the preliminary small-scale pilot test data.

5. As an example, the following culture conditions was used to ferment *Rhodococcus ruber*:

(1) The Culture Medium Composition Comprising:

peptone, broth, sodium chloride, phosphate, glycerin (and, optionally agar, when in solid culture).

(2) Parameters of the Culture Method:

After the working strain was recovered, it was transferred to a solid culture medium for 3 to 5 days, and then transferred to liquid culture (30 to 37° C., maintained for 3 to 5 days). The fed-batch semi-continuous mode or the batch mode can be used. The pH, bacterial density, dissolved oxygen and carbon source consumption were monitored during culture.

Preparation Example 2. Bacteria Disruption

The bacteria obtained in Preparation Example 1 were collected and the cells were disrupted (for example, but not limited to sonication). Any appropriate well-known method in the art were also allowed to disrupt the bacteria, such as CN101250490A or CN101323865A.

The disruption state was checked under a microscope. There should not be more than 5 visible bacteria in each visual field. The disruption was considered as qualified when several (10 to 30) visual fields checked met this standard.

Preparation Example 3. Removal of Nucleic Acids, Lipids, Proteins and Cell Membranes 1. Removal of Nucleic Acids:

The supernatant after disruption was centrifuged. DNase and RNase were added to the obtained precipitate, and nucleic acids were removed according to the operation recommended by the supplier of the enzymes.

2. Removal of Proteins:

Commonly used protease (such as trypsin) was added to the precipitate, and proteins were removed according to the operation recommended by the supplier of the enzyme.

3. Removal of Lipids:

Organic reagents (for example, but not limited to, any one of acetone, ether and ethanol or combination thereof) were added to the precipitate, and lipids were removed according to conventional operations in the art.

4. Removal of Cell Membranes:

Triton X-100 was added to the precipitate, and the precipitate was collected by centrifugation according to conventional operations in the art, and rinsed with PBS.

It should be understood that among the above steps for removing impurities; the skilled person can adjust their orders of steps to make them compatible with each other. After removing the non-cell wall components, the precipitate was reconstituted in water for injection, and then set aside till use. Optionally, it could be sterilized at 115° C. for 20 to 30 minutes as the stock solution of the cell wall skeleton (mainly containing the cell wall skeleton and components thereof).

5. Yield

A total of 653 mL of bacterial liquid (after disruption) was collected from 159 Kolle flasks. The wet weight yield was 138 g; the cell wall skeleton yield was about 0.87 g/Kolle flask.

Preparation Example 4. Preparation Methods of the Pharmaceutical Compositions

1. Excipients (such as dextran 40, mannitol or trehalose) were added to the product obtained in Preparation Example 3. The resulting product was referred to the pharmaceutical composition, after filling into aliquots.

TABLE 1

The pharmaceutical composition can be formulated in various forms

| Composition | Capacity of each vial | Components | |
|---|---|---|---|
| Composition 1 | 2 mL | Active ingredient | 60 μg |
| | | Dextran 40 | 15 mg |
| Composition 2 | 2 mL | Active ingredient | 60 μg |
| | | Dextran 40 | 12 mg |
| Composition 3 | 2 mL | Active ingredient | 120 μg |
| | | Dextran 40 | 36 mg |
| Composition 4 | 2 mL | Active ingredient | 60 μg |
| | | Trehalose | 12 mg |
| Composition 5 | 2 mL | Active ingredient | 120 μg |
| | | Trehalose | 36 mg |
| Composition 6 | 2 mL | Active ingredient | 120 μg |
| | | Mannitol | 36 mg |
| Composition 7 | 2 mL | Active ingredient | 60 μg |
| | | Mannitol | 12 mg |

2. The product obtained in Preparation Example 3 (active ingredient 60 μg to 120 μg) was coated on the dressing to prepare a medical device for external use.

3. The pharmaceutical compositions in step 1 were lyophilized to prepare lyophilized powders (numbered as compositions 1 to 7, respectively).

4. Quality inspection (lyophilized powder composition 1 was taken as an example).

TABLE 2

Quality inspection items

| | |
|---|---|
| Appearance | White unconsolidated solid or powder |
| Water content | ≤6% |
| Solubility | the product was deemed as being qualified, if it dissolved within 1 minute when 2.0 mL of NaCl injection was added |
| Identification of saccharide | The solution was blue-green in color |
| Content of muramic acid | 2.0 μg/vial (criteria: ≥1.0 μg/vial) |
| Residual amount of proteins | 0.4 μg/vial (criteria: ≤9.0 μg/vial) |
| Residual amount of RNA | 0.8% (criteria: not more than 5%) |
| Residual amount of DNA | 0.9% (criteria: not more than 5%) |
| Residual amount of Triton X-100 | Undetectable (criteria: not more than 5%) |
| Residual amount of lipids | 3.8% (criteria: not more than 5%) |
| Phagocytosis rate | 75% (criteria: ≥40%) |
| Phagocytic index | 1.05 (criteria: ≥0.50) |
| Abnormal toxicity in mice | All the mice should survive and have no abnormal reactions during the observation period. The composition was considered as qualified if the body weight of each mouse increased at the due date. |
| Abnormal toxicity in guinea pigs | All the guinea pigs should survive and have no abnormal reactions during the observation period. The composition was considered as qualified if the body weight of each guinea pig increased at the due date. |

TEST EXAMPLES

Test Example 1. Pharmacological Tests

1. After intravenous injection (equivalent to 20, 40 and 80 times of human clinical dose), the blood pressure, respiration, heart rate and electrocardiogram of the anesthetized cats were monitored, and the compositions had no significant effect;

2. After intravenous injection (equivalent to 1000 times of the human clinical dose), the compositions had no significant effect on the coordinated movement and learning and memory function of mice.

It can be seen that the pharmaceutical compositions of the present invention (composition 1 to composition 7) had no significant effect on the mental state, nervous system, cardiovascular system and respiratory system of animals.

Test Example 2. Safety Tests

1. Sterility Test:

The results were negative, proving the sterility of the compositions.

2. Acute Toxicity Test in Mice:

The experimental group was administrated by subcutaneous injection and intraperitoneal injection, and the dose was 5 times human dose. The control group was treated with sterile saline 0.5 mL/vial. The animals were continuously observed for 7 to 8 days. The mice were in good condition and had no abnormality in their body weight or their organs.

3. Long-Term Toxicity Test:

The compositions were vaginally administered for once per day for three months, at a dose which is equivalent to 30 times of the clinical dose. No toxic effects were observed in dogs; the electrocardiograms and blood biochemical indicators were within the normal range. Two weeks after cessation of administration, no delayed toxicity was observed (composition 1 to composition 7).

Test Example 3. Stability Tests

The pharmaceutical compositions were placed at room temperature (18 to 25° C.) for 0, 1, 2, 3, 8, 14 and 21 months, and the alanine content, muramic acid content, phagocytosis rate and phagocytic index had no statistically significant difference compared to those at the start of the test (three batches were tested).

In summary, the pharmaceutical composition of the lyophilized powder formulation can be stored stably for 24 months (composition 1 to composition 7).

Test Example 4. Phagocytosis Tests

Macrophages are the main cells of the mononuclear phagocyte system. The activation of phagocytes after antigen stimulation can significantly enhance the phagocytic function. After inducing the production of peritoneal macrophages in the mice, the mice were intraperitoneally injected with chicken red blood cells. After 30 minutes, the mice were sacrificed and the peritoneal fluid was collected for staining. The percentage of phagocytes that phagocytized red blood cells was counted under a microscope to determine their killing ability, indirectly indicating the non-specific immunity level of the body.

Composition 1 of the present application was used for testing. Its phagocytosis rate was 75% and phagocytic index was 1.05. While, the phagocytosis rate and phagocytic index of the negative control (excipient) and blank control (saline) were all relatively low. These results show that the cell wall skeleton of the present application has a strong ability to promote immunophagocytosis.

Effect Example (Treatment of Oral Lichen Planus)
1. Criteria for Diagnosis, Inclusion and Exclusion of Cases
1.1 Criteria for Diagnosis Diagnosis was performed according to WHO 2003 diagnostic criteria for oral lichen planus (Meij EHVD, Waal IVD. Lack of clinicopathologic correlation in the diagnosis of oral lichen planus based on the presently available diagnostic criteria and suggestions for modifications. Journal of Oral Pathology & Medicine, 2003, 32(9):507-512).

1.2 Criteria for Inclusion
① Patients diagnosed as erosive oral lichen planus based on medical history, clinical manifestations and pathology;
② the age of onset is 18-75 years old, and relevant treatment drugs have not been taken within 1 month before the onset;
③ patients without visual field defects, fundus lesions and systemic diseases (Liu Qinglan et al., The effects and safety of triamcinolone acetonide oral ointment in the treatment of erosive oral lichen planus. Journal of Practical Stomatology, 2017, 33(04): 536-540).

1.3 Criteria for Exclusion
① patients with other confirmed oral mucosal diseases;
② patients with uncontrolled diabetes, tumors, etc.;
③ patients who have been administrated with antibiotics within 1 month or immune formulations within 3 months;
④ patients who may have lichen-like reactions induced by some drugs or amalgam fillings;
⑤ patients with allergic constitution and a history of allergies to drugs and food;
⑥ patients who are unable to follow the doctor's prescription or have incomplete records of the test process (which affect determination of the therapeutic effect) (Gorouhi F et al., Randomized trial of pimecrolimus cream versus triamcinolone acetonide paste in the treatment of oral lichen planus, Journal of the American Academy of Dermatology, 2007, 57(5):806-813).

1.4 Subjects to be Studied

Patients with erosive oral lichen planus that met the above diagnostic criteria were selected. A randomized, double-blind, placebo-controlled clinical trial method was adopted, and the trial group and the control group were divided according to the random numbering. The research protocol was submitted to and approved by the ethics committee. All test subjects signed informed consent forms.

1.5 Sample Size

The effective cases for small sample size collected in this test should not be less than 60, including 30 cases in the experimental group and 30 cases in the control group (considering the dropout rate was about 20%, it was recommended to collect 75 cases).

2. Treatment Methods and Groups
2.1 Treatment Group

The lyophilized powder of composition 1 was topically applied to the erosion surface of the patient once every other day, 1 vial (60 μg) each time, before going to bed, and combined with saline mouthwash for 28 days. Method of application: before each administration, the patient's mouth was rinsed by saline, then the erosion surface was wiped clean with a cotton swab, and the lyophilized powder was applied onto the erosion surface of the patient with erosive oral lichen planus for 2 hours.

2.2 Control Group

The placebo (excipient only) was topically applied to the erosion surface of the patient once every other day, 1 vial each time, before going to bed, and combined with saline mouthwash for 28 days. Method of application: the same as above.

3. Efficacy Evaluation Indicators
3.1 Scoring of Signs

REU scoring system was applied for scoring of signs (Table 3) (Park H K et al., Oral lichen planus: REU scoring system correlates with pain, Oral Surgery Oral Medicine Oral Pathology Oral Radiology, 2012, 114(1): 75-82).

TABLE 3

| REU scoring system of oral lichen planus | |
|---|---|
| Clinical classification | Score |
| Reticular/hyperkeratotic (R) | 0 for no white stripes; |
|  | 1 for with white stripes or keratotic plaques; |
| Erosive/erythematous (E) | 0 for no lesion; |
|  | 1 for lesion < 100 mm$^2$; |
|  | 2 for lesion of 100 to 300 mm$^2$; |
|  | 3 for lesion > 300 mm$^2$ |
| Ulcerative (U) | 0 for no lesion; |
|  | 1 for lesion < 100 mm$^2$; |
|  | 2 for lesion of 100 to 300 mm$^2$; |
|  | 3 for lesion >300 mm$^2$ |
| Total score (Σ) | Σ = ΣR + Σ(E × 1.5) + Σ(U × 2.0) |

3.2 Scoring of Pain Symptoms

The subjective indicators were based on visual analogue scale (VAS), dividing into 10 grades. The degree of pain was recorded as 1 to 10 points in a subject's diary card, and was evaluated by patient in the morning after administration every day (Table 4).

TABLE 4

VAS scale for patients with oral lichen planus

| Degree of pain | VAS score | Score of symptoms |
| --- | --- | --- |
| No pain | 0 | 0 |
| Mild pain | 1 to 3 | 1 |
| Moderate pain | 4 to 6 | 2 |
| Severe pain | 7 to 10 | 3 |

3.3 OHIP-14 Scale

The OHIP-14 scale consists of 14 items in 7 parts (namely, restriction of oral function, physical pain, psychological discomfort, physical disorder, psychological disorder, social disorder and disability). Each item in the scale is divided into 5 levels and has a corresponding score (0 for never, 1 for rarely, 2 for sometimes, 3 for often, and 4 for very often). The total score is 0 to 56 points. The lower the value is, the better the oral health condition.

In this trial, the scale was filled by the patient during the first visit and the follow-ups in the $1^{st}$, $2^{nd}$ and $4^{th}$ weeks after administration (see Sampogna F et al., Comparison of patients' and providers' severity evaluation of oral mucosal conditions. Journal of the American Academy of Dermatology, 2011, 65(1): 69-76).

3.4 Criteria for Efficacy Evaluation

| | |
| --- | --- |
| Significantly effective | The congestion and erosion disappeared completely after treatment, and the white stripes were absent or slight (score of signs was 0 or 1 point); the pain disappeared completely (score of symptoms was 0 point); |
| Effective | The congestion and erosion were reduced after treatment (score of signs decreased); the pain was alleviated (score of symptoms decreased); |
| Invalid | The congestion and erosion were unchanged or increased after treatment (score of signs unchanged or increased); the pain was not alleviated or increased after treatment (score of symptoms unchanged or increased); |

Total efficacy rate=(significantly effective+effective)×number of cases/total number of cases× 100%.

See Zhou Gang et al., Oral lichen planus (atrophic, erosive) efficacy evaluation criteria, Chinese Journal of Stomatology, 2005, 40(2): 92-93.

3.5 Safety Evaluation

Laboratory indicators: Blood cell analysis, liver and kidney function and blood sugar detection.

3.6 Time Period of Efficacy Evaluation

The score of symptoms and score of signs after 1, 2, and 4 weeks of administration and the OHIP-14 scale score were observed to evaluate the efficacy after 4 weeks of treatment, and whether any side effect occurred during the observation period.

3.7 Statistical Methods

SPSS 24.0 statistical software was used for data processing and analysis. The chi-square test was used for the comparison of enumeration data. The rank sum test or the group t test was used for the comparison of measurement data between groups. The rank sum test or paired t test was used for self-comparison before and after treatment within the group. The difference was deemed as statistically significant when P<0.05 (Huang Yueqin, Clinical Epidemiology, People's Medical Publishing House, 2014).

4. Results 4.1 General Information of the Subjects to be Studied

A total of 66 patients were enrolled in this trial, of which 6 were lost to follow-up (patients were unable to apply the medicament due to business trips), and 60 completed the observation.

Experimental group: 30 subjects, 9 males and 21 females;
Control group (placebo): 30 subjects, 10 males and 20 females.

There was no significant difference in the general condition and oral hygiene status between the two groups of patients, P>0.05.

TABLE 5

Baseline characteristics of the population studied in the experimental group and the control group

| Item | Treatment group | Control group | P |
| --- | --- | --- | --- |
| Age | 48.9 ± 9.60 | 51.23 ± 8.42 | 0.834 |
| Female % | 21 (70.00%) | 20 (66.67%) | 0.903 |
| Course of disease | 6.26 ± 4.96 | 5.93 ± 5.22 | 0.462 |
| VAS score | 2.11 ± 0.67 | 1.73 ± 0.56 | 0.238 |
| OHIP score | 18.99 ± 9.43 | 17.82 ± 10.24 | 0.434 |
| REU score | 3.08 ± 0.74 | 2.41 ± 0.23 | 0.154 |

The data is represented as x ± s (n = 2).

4.2 Effectiveness Analysis (1) Comparison of REU Scores of Signs Between the Two Groups After 1, 2 and 4 weeks of treatment for patients in the experimental group and the control group, the differences in the scores of signs between the experimental group before and after treatment were statistically significant (P<0.05); the differences in the scores of signs between the two groups after 4 weeks of treatment were statistically significant (P<0.05) (Table 6).

TABLE 6

Comparison of REU scores of signs between the two groups

| Item | Week 0 | Week 1 | Week 2 | Week 4 | P value |
| --- | --- | --- | --- | --- | --- |
| Experimental group | 3.08 ± 0.74 | 2.37 ± 1.23 | 1.92 ± 1.13 | 1.48 ± 0.96 | 0.000* |
| Control group | 2.41 ± 0.23 | 2.36 ± 0.65 | 2.31 ± 0.59 | 2.26 ± 1.19 | 0.063* |
| P | 0.154+ | 0.821+ | 0.182+ | 0.001+ | |

*Comparison within the group, before and after treatment;
+Comparison between groups after treatment; the data is represented as x ± s (n = 2).

(2) Comparison of Scores of Symptoms Between the Two Groups

After 1, 2 and 4 weeks of treatment for patients in the experimental group and the control group, the differences in the scores of symptoms within the experimental group were statistically significant (P<0.05), and the differences in the scores of symptoms between the two groups after treatment were statistically significant (P<0.05) (Table 7).

TABLE 7

Comparison of VAS scores between the two groups

| Item | Week 0 | Week 1 | Week 2 | Week 4 | P value |
|---|---|---|---|---|---|
| Experimental group | 2.11 ± 0.67 | 1.21 ± 0.76 | 0.70 ± 0.54 | 0.32 ± 0.63 | 0.000* |
| Control group | 1.73 ± 0.56 | 1.67 ± 0.76 | 1.60 ± 0.93 | 1.56 ± 0.73 | 0.041* |
| P | 0.238[+] | 0.004[+] | 0.000[+] | 0.000[+] | |

*Comparison within the group, before and after treatment;
[+]Comparison between groups after treatment; the data is represented as x ± s (n = 2).

(3) Comparison of OHIP-14 Scale Scores Between the Two Groups

After 1, 2 and 4 weeks of treatment for patients in the experimental group and the control group, the OHIP-14 scale scores of the experimental group significantly decreased after treatment and were statistically significant ($P<0.05$), and the differences in the OHIP-14 scale scores between the two groups after treatment were statistically significant ($P<0.05$) (Table 8).

TABLE 8

Comparison of OHIP-14 scale scores between the two groups

| Item | Week 0 | Week 1 | Week 2 | Week 4 | P value |
|---|---|---|---|---|---|
| Experimental group | 18.99 ± 9.43 | 10.61 ± 4.97 | 8.32 ± 6.89 | 5.21 ± 3.99 | 0.000* |
| Control group | 17.82 ± 10.24 | 16.33 ± 10.22 | 15.55 ± 12.71 | 14.56 ± 11.28 | 0.001* |
| P | 0.434[+] | 0.013[+] | 0.000[+] | 0.000[+] | |

*Comparison within the group, before and after treatment;
[+]Comparison between groups after treatment; the data is represented as x ± s (n = 2).

(4) Comparison of the Efficacy Rates Between the Two Groups after Treatment

After 2 weeks of treatment and 4 weeks of treatment, the total efficacy rates of the experimental group were 70.00% and 86.67%, respectively, and the total efficacy rates of the control group were 23.33% and 26.67%, respectively.

4.3 Safety Analysis

After 4 weeks of administration, there were no statistically significant differences between the experimental group and the control group in blood cell analysis, liver and kidney function, and blood glucose examination ($P>0.05$). No irritation or allergic reactions occurred in patients during administration, and no side effects occurred.

4.4 Follow-Up after Cessation of Administration 12 patients in the experimental group were followed up for 4 weeks after cessation of administration, and it was found that only 2 patients had recurrence of erosions. No irritation or allergic reactions occurred in patients after administration, and no side effects occurred.

The study found that the total efficacy rates of the experimental group after administration were significantly higher than those of the control group. The erosion area, degree of pain and degree of oral health impact of the experimental group were all reduced after 1, 2 and 4 weeks of treatment. In the results of the study, the degree of pain and degree of oral health impact of the control group were slightly reduced than before treatment, which may be due to the psychological effect of placebo.

*Rhodococcus ruber* cell wall skeleton used in the treatment of erosive lichen planus can effectively reduce the erosion area of OLP, reduce the degree of pain and show relatively favorable clinical effects after administration. There was no statistical difference between its safety indicators and those of the control group.

What is claimed:

1. A method for preventing and/or treating erosive oral lichen planus in a subject in need thereof, comprising topically administering to the subject a therapeutically effective amount of *Rhodococcus ruber* cell wall skeleton.

2. The method of claim 1, wherein the *Rhodococcus ruber* cell wall skeleton is derived from the isolated *Rhodococcus ruber* deposited with CGMCC with Accession No. 17431.

3. The method of claim 1, wherein the therapeutically effective amount is in a unit dose of 1 μg to 1000 μg.

4. The method of claim 1, wherein a therapeutically effective amount of *Rhodococcus ruber* cell wall skeleton is administered at a frequency selected from the group consisting of: 1 to 3 times per day, 1 to 6 times in two days, 1 to 9 times in three days, 1 to 14 times per week, and 1 to 60 times per month.

* * * * *

SEQUENCE LISTING

```
<160> NUMBER OF SEQ ID NOS: 1

<210> SEQ ID NO 1
<211> LENGTH: 1364
<212> TYPE: DNA
<213> ORGANISM: Rhodococcus ruber

<400> SEQUENCE: 1
ggttaggcca ccggcttcgg gtgttaccga ctttcatgac gtgacgggcg gtgtgtacaa     60
ggcccgggaa cgtattcacc gcagcgttgc tgatctgcga ttactagcga ctccgacttc    120
acggggtcga gttgcagacc ccgatccgaa ctgagaccgg ctttaaggga ttcgctccac    180
ctcgcggtat cgcagccctc tgtaccggcc attgtagcat gtgtgaagcc ctggacataa    240
```

```
-continued ggggcatgat gacttgacgt cgtccccacc ttcctccgag ttgaccccgg cagtctcctg    300
cgagtcccca ccattacgtg ctggcaacac aggacaaggg ttgcgctcgt tgcgggactt    360
aacccaacat ctcacgacac gagctgacga cagccatgca ccacctgtac accgaccaca    420
agggaaaccc catctctggg gcggtccggt gtatgtcaaa cccaggtaag gttcttcgcg    480
ttgcatcgaa ttaatccaca tgctccgccg cttgtgcggg cccccgtcaa ttcctttgag    540
ttttagcctt gcggccgtac tccccaggcg gggcgcttaa tgcgttagct acggcacgga    600
tcccgtggaa ggaaacccac acctagcgcc caccgtttac ggcgtggact accagggtat    660
ctaatcctgt tcgctaccca cgctttcgct cctcagcgtc agttactgcc cagagacccg    720
ccttcgccac cggtgttcct cctgatatct gcgcatttca ccgctacacc aggaattcca    780
gtctcccctg cagtactcaa gtctgcccgt atcgcctgca agcccgcagt tgagctgcgg    840
gttttcacag acgacgcgac aaaccgccta cagctcttta cgcccagtaa ttccggacaa    900
cgctcgcacc ctacgtatta ccgcggctgc tggcacgtag ttggccggtg cttcttctgt    960
acctaccgtc acttgcgctt cgtcggtact gaaagaggtt tacaacccga aggccgtcat   1020
ccctcacgcg gcgtcgctgc atcaggcttg cgcccattgt gcaatattcc ccactgctgc   1080
ctcccgtagg agtctgggcc gtgtctcagt cccagtgtgg ccggtcgccc tctcaggccg   1140
gctacccgtc gtcgccttgg tgggccgtta ccccaccaac aagctgatag gccgcgggcc   1200
catcctgcac cggaaaacct ttccaccccg aacatgcatc ccgaggtcct atccggtatt   1260
agacccagtt tcccaggctt atcccgaagt gcagggcaga tcacccacgt gttactcacc   1320
cgttcgccac taatccaccc agcaagctgg cttcatcgtt cgac                    1364
```